United States Patent [19]

Matsumoto

[11] Patent Number: 5,200,322
[45] Date of Patent: Apr. 6, 1993

[54] METHOD FOR ASSAYING PROTEIN C AND MEASURING KIT FOR THE SAME

[75] Inventor: Kenji Matsumoto, Hyogo, Japan

[73] Assignee: Nippon Zoki Pharmaceutical Co., Ltd., Japan

[21] Appl. No.: 662,497

[22] Filed: Feb. 28, 1991

Related U.S. Application Data

[63] Continuation of Ser. No. 97,732, Sep. 17, 1987, abandoned.

[30] Foreign Application Priority Data

Sep. 19, 1986 [JP] Japan ................... 61-222294
Feb. 18, 1987 [JP] Japan ................... 62-36739

[51] Int. Cl.$^5$ ................... C12Q 1/56; G01N 33/86
[52] U.S. Cl. ................... 435/13; 435/23; 435/184; 435/810; 436/69; 436/175; 436/800; 436/825
[58] Field of Search ................... 435/13, 23, 184, 810; 436/69, 175, 800, 825

[56] References Cited

U.S. PATENT DOCUMENTS 4,258,192 3/1981 Okawato et al. ................... 546/166
4,537,896 8/1985 Claeson et al. ................... 514/330
4,698,298 10/1987 Dedieu et al. ................... 435/7

FOREIGN PATENT DOCUMENTS 59-175898 10/1984 Japan.
60-149399 8/1985 Japan.
2099580 12/1982 United Kingdom.

OTHER PUBLICATIONS

Ohno et al., *Journal of Biochemistry*, vol. 90, pp. 1387-1395, 1981.
Triplett, *Clinical in Laboratory Medicine*, vol. 4, No. 2, "Coagulation" W. B. Saunders Company, (Philadelphia), 1984.
Wagner et al., *Pharmazie*, vol. 39, No. 4, pp. 226-230, 1984 (Chemical Abstract 101: 211666p).
Stocker et al., Behring Inst. Mitt. 79: 37-47 "Protein C Activators In Snake Venoms" Feb. 1986.
Koide, T., *J. Biochem.*, vol. 86, No. 6, pp. 1841-1850 (1979).
"Cytosolic and Mitochondrial Isoenzymes of Glutamic-Oxalacetic Transaminase from Human Heart"; Teranishi et al.; The Journal of Biological Chemistry, vol. 243, No. 24, Dec. 25, 1978, pp. 8842-8847.

*Primary Examiner*—Johnnie R. Brown
*Assistant Examiner*—Abdel A. Mohamed
*Attorney, Agent, or Firm*—Oliff & Berridge

[57] ABSTRACT

An enzymic method for assaying protein C by the use of a synthetic peptide substrate, wherein the action of interfering substances against said peptide substrate are specifically inhibited, and a measuring kit for the same.

11 Claims, 2 Drawing Sheets

METHOD FOR ASSAYING PROTEIN C AND MEASURING KIT FOR THE SAME

This is a continuation of application Ser. No. 07/097,732 filed Sep. 17, 1987, now abandoned.

BACKGROUND OF THE INVENTION

This invention relates to a method for assaying protein C (hereinafter abbreviated as PC) and to a kit for measuring PC activity. More particularly, it relates to an enzymatic method for directly measuring the activity of PC without isolating it from the plasma, and to a measuring kit for the same.

PC is a vitamin-K-dependent plasma protein, which can be converted to activated protein C (hereinafter abbreviated as PCa) by the action of thrombin-thrombomodulin complex in the presence of $Ca^{2+}$ ions. PCa is receiving attention as a plasma protein that is capable of selectively degrading blood coagulation factors V and VIII, thus exhibiting a powerful anti-coagulant action, and of liberating vascular plasminogen activator, thereby accelerating fibrinolysis.

It is known that PC level in the blood decreases as a result of disseminated intravascular coagulation syndrome (DIC) and hepatic diseases, such as hepatocirrhosis and chronic hepatitis. Recently a new PC deficiency disease accompanied by multiple thrombosis was reported. In addition, the effect of PC content upon the efficacy of blood coagulation factor (e.g., factor IX) preparations has been a subject of major concern.

Under the circumstances, there has been a demand for a simple method for correctly assaying PC in the plasma to diagnose the aforementioned PC deficiency disease, DIC and hepatic diseases, and to check the efficacy of various blood coagulation factor preparations.

Several methods are now used for quantitative analysis of PC, including the enzymatic method which employs a synthetic peptide substrate specific to PCa. But direct measurement of the activity of PC in the plasma by this type of method has been difficult, because the blood contains PC inhibitors and other interfering substances which, during activity measurement, act upon the synthetic peptide substrate without being inhibited by antithrombin III.

It is therefore necessary to previously isolate PC from the plasma by means of an antibody column or an adsorbent. But such a pretreatment, which requires a considerable amount of sample blood and needs much time and labor, is unsuitable for rapid treatment of a vast number of samples. In addition, the use of an adsorbent suffers from the low recovery rate of PC, while the use of an antibody column is very costly, although the PC recovery rate is satisfactory.

A biological method utilizing the anticoagulating action of PC is also known, in which PC, after being activated with snake venom, is added to a blood coagulation system and its action to prolong the coagulation time is measured. But the sensitivity of this method is not so high.

Immunological methods are also known, in which the amount of PC antigen is measured through an antigen-antibody reaction using a polyclonal or monoclonal antibody (the radioimmunoassay, enzyme immunoassay and Laurell's method). The techniques of this type are capable of correctly measuring the amount of PC antigen, but the disadvantages are that the antibody used is very costly, a long time is needed for measurement, and it is impossible to judge whether the PC tested has normal activity or not.

As a result of intensive studies to establish a new analytical method for PC free of the above-mentioned problems, we have succeeded in accomplishing this invention.

SUMMARY OF THE INVENTION

An object of this invention is to provide a new and useful method of assaying PC.

A further object of this invention is to provide an enzymatic method for measuring PC activity which allows treatment of a vast number of samples in a short time by simple operations without pretreatment to isolate PC from the plasma.

Another object of this invention is to provide a measuring kit to be used in the above-mentioned method.

The PC assaying method of this invention is an enzymatic method of measuring PC activity by the use of a synthetic peptide substrate, wherein interfering substances acting upon said peptide substrate are specifically inhibited.

The PC activity measuring kit of this invention comprises (A) a PC activator, (B) antithrombin III, (C) a low-molecular-weight thrombin inhibitor, and (D) a synthetic peptide substrate.

BREIF DESCRIPTION OF THE DRAWINGS

FIG. 1 shows a calibration curve prepared according to the data obtained in the Example of this invention, and FIG. 2 is a graph illustrating a relationship between the method of this invention and the enzyme immunoasay (EIA).

DETAILED DESCRIPTION OF THE INVENTION

Figure 1:
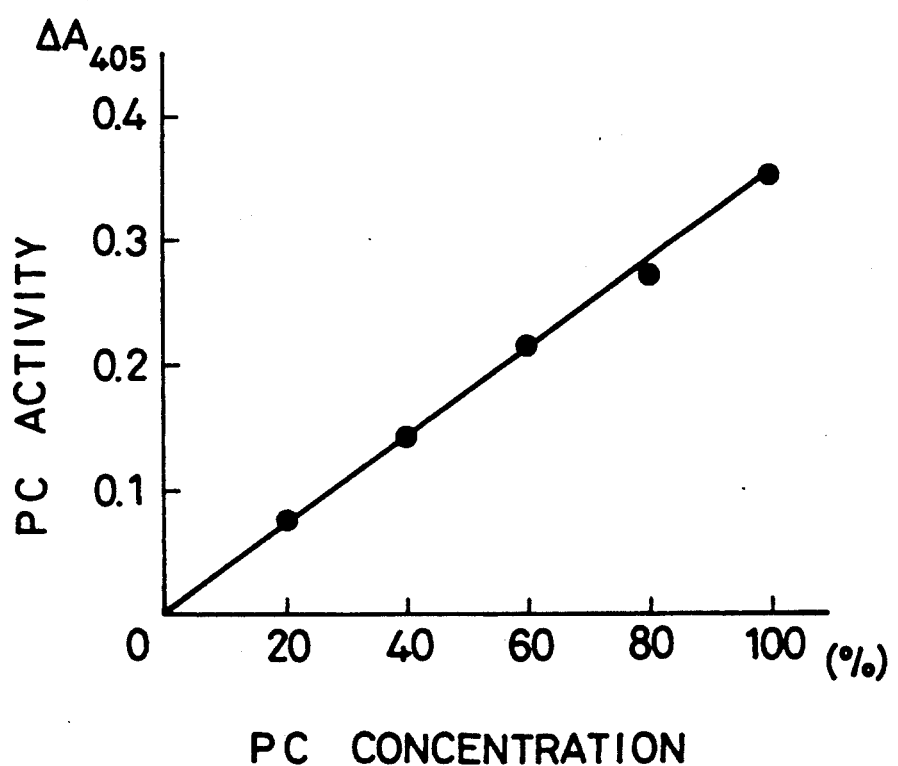

In the PC assaying method of this invention, interfering substances (other than PCa) contained in the plasma and acting upon the synthetic peptide substrate are inhibited, thereby allowing direct measurement of PC activity without isolating it from the plasma.

The method of this invention may be practiced according to the following steps:

(a) A PC activator is added to diluted plasma to form PCa.

(b) An inhibitor against interfering substances (other than PCa) contained in the plasma and acting upon the synthetic peptide substrate is added.

(c) A synthetic peptide substrate is then added, and the decomposition product formed by the action of PCa is colorimetrically or fluorometrically measured, thereby determining the amount of PC.

The method of this invention is described below in more detail.

1) Plasma dilution rate

Since the plasma contains the endogenous PC inhibitors which inhibit the action of PCa, PCa activity cannot be correctly determined without taking suitable measures to eliminate its effect. In the method of this invention, the effect of PC inhibitor can be avoided by diluting the plasma sample by a factor of 10 or more, preferably by a factor of 10 to 30.

The plasma used in this invention may comprise any plasma sample prepared by commonly employed methods, for example, citrate-containing plasma prepared by taking a blood sample in the presence of sodium citrate, followed by centrifugal separation.

2) Buffer solution

A buffer solution adjusted to a pH level near the conditions in living bodies by using a buffering agent, such as Tris-HCl, should preferably be used to dilute the plasma. Sodium chloride and other salts may also be added to the solution, as required, to bring it more close to the conditions in living bodies. In addition, protease inhibitors, such as soybean trypsin inhibitor (SBTI) and aprotinin, may also be added in amounts that will not affect PCa activity in order to suppress the actions of various proteases in the plasma.

Furthermore, a stabilizer, such as bovine serum albumin (BSA), may also be added to prevent precipitation of proteins under weakly acidic conditions at the termination of the reaction.

3) PC activator

Thrombin-thrombomodulin complex, snake venom and others may be mentioned as the PC activator, but use of thrombin-thrombomodulin complex is preferable in terms of physiologically natural conditions. It may be added in the form of complex, or thrombin and thrombomodulin may be added separately.

Since activation of PC requires the presence of $Ca^{2+}$ ions, it is preferable to add these ions to the buffer solution or to the solution of PC activator in an amount that will give optimum concentration in the PC activation system.

4) Inhibitor against interfering substances

Thrombin added to activate PC also acts upon the synthetic peptide substrate, and hence interferes with the measurement of PC activity. It is therefore necessary to add an inhibitor against thrombin after PC has been activated. This inhibitor must preferably be such that it inhibits the action of thrombin and shows no effect upon PCa. Antithrombin III may be used for this purpose; in actual practice, it is preferable to use heparin in combination because it markedly accelerates the action of antithrombin III.

However, addition of antithrombin III alone cannot inhibit the activity of the other interfering substances contained in the plasma. In fact, measurement of PC activity by the use of a synthetic substrate in combination with antithrombin III/heparin alone gave an unusually high apparent PC activity—multi-hundred times as high as the estimated level obtained by the immunological method. Thus, previous isolation of PC by the use of an antibody column or an adsorbent, or other intricate pretreatment, is indispensable when measuring PC activity by addition of antithrombin III alone.

Assiduous studies in pursuit of an effective method for inhibiting interfering substances acting upon the synthetic substrate have led us to find that this object can be achieved by using a low-molecular-weight thrombin inhibitor in combination with high-molecular-weight substances like anti-thrombin III, and to succeed in correctly measuring PC activity without the need for isolation and purification of PC.

The low-molecular-weight thrombin inhibitors that can be used in the method of this invention are preferably those which show no effect upon the activity of PCa. These include thrombin inhibitors with a molecular weight not higher than 2,000, more preferably, not higher than 1,000. Illustrative examples are N-arylsulfonyl-L-arginine derivatives, such as (2R,4R)-1-[N²-(3-methyl-1,2,3,4-tetrahydro-8-quinolinesulfonyl)-L-arginyl]-4-methyl-2-piperidinecarboxylic acid (Compound 1) and dansylarginine N-(3-ethyl-1,5-pentanediyl)amide (Compound 2) [J. Med. Chem., 23, 827–836 and 1293–1299 (1980), and others]; and N-arylsulfonylglycyl-amidinophenylalanine derivatives, such as $N^{\alpha}$-aryl-(2-naphthylsulfonylglycyl)-4-amidinophenylalanine-piperidide (Compound 3) [Thromb. Res., 36, No. 5, 457–465 (1984)].

5) Synthetic peptide substrate

Synthetic peptide substrates commonly used in conventional methods for measuring enzymatic activity can be employed in the method of this invention. Illustrative examples are color-developing symthetic substrates, such as Pyr-Pro-Arg-pNA (S-2366: pyroglutamyl-prolyl-arginyl-p-nitroanilide), D-Val-Leu-Arg-pNA (S-2266: D-valyl-leucyl-arginyl-p-nitroanilide) and D-Phe-Pip-Arg-pNA (S-2238: D-phenylalanyl-piperidino-arginyl-p-nitroanilide); and fluorescent synthetic peptide substrates, such as Boc-Leu-Ser-Thr-Arg-MCA (3112-V: t-butoxycarbonylleucyl-seryl-threonyl-arginyl-4-methylcoumalinamide).

The enzymatic reaction between PCa and a synthetic peptide substrate can be terminated by making the reaction system weakly acidic. Hence a weak acid, such as citric and acetic acids, is preferably used as the terminator.

This invention also relates to a PC activity measuring kit. As may be seen from the foregoing, this kit comprises (A) a PC activator, (B) antithrombin III, (C) a low-molecular thrombin inhibitor, and (D) a synthetic peptide substrate.

Use of this PC activity measuring kit may be summarized as follows:

(a) A PC activator is added to diluted plasma to form PCa.

(b) The inhibitor against the action of interfering substances other than PCa (antithrombin III and a low-molecular thrombin inhibitor) is further added.

(c) A synthetic peptide substrate is then added to measure PC activity enzymatically. After termination of the reaction, the decomposition product formed by the action of PCa is colorimetrically or fluorometrically measured, thereby determining the amount of PC.

The following Example will further illustrate the invention but is not intended to limit its scope.

EXAMPLE

Kit Components (Amounts in Each Vial)

(A) Thrombin-thrombomodulin complex (freeze-dried product) 10 U/ml Thrombin/0.85 nmol/ml thrombomodulin Dissolve in 4 ml distilled water for use.

(B) Antithrombin III/heparin complex (freeze-dried product) 25 U/ml Antithrombin III/100 U/ml heparin Dissolve in 4 ml of the following solution for use.

(C) Aqueous solution of Compound 1 5 ml (100 μg/ml)

(D) S-2366 (freeze-dried product)

Dissolve in 4 ml distilled water for use (3 mM aqueous solution).

Operating Procedure (a) Plasma being tested was diluted 1:20 with the buffer solution (50 mM Tris-HCl (pH 8.0)/0.1M NaCl/1 mM $CaCl_2$/0.1% BSA/0.1 mg/ml SBTI), the diluted solution was incubated at 56° C. for five minutes, the fibrin which separated out was removed by centrifugation, and 200 μl of the supernatant was collected.

(b) The solution of thrombin/thrombomodulin complex (100 μl) was added, and the mixture was incubated at 37° C. for thirty minutes.

(c) The solution of antithrombin III/heparin/Compound 1 (100 μl) was added, and the mixture was incubated at 37° C. for five minutes.

(d) The solution of S-2366 (100 μl) was added, and the mixture was incubated at 37° C. for 30 minutes.

(e) A 2% aqueous solution of citric acid was added, and the absorbance at 405 nm was measured.

Thus, forty test samples can be assayed by one set of the measuring kit shown above. It is needless to say that various types of kits may also be prepared to meet particular needs by changing the amount of each component in each vial, by adjusting the plasma dilution rate and by appropriately altering the scale of the whole system.

Calibration Curve

A calibration curve prepared from pooled plasma of normal human adults is shown in FIG. 1.

As is apparent from the figure, a linear relationship holds over the PC concentration range from 0 to 100%, indicating the high accuracy of PC activity determination by the use of the measuring kit of this invention.

Described below is the result of our studies on various measuring conditions with the kit of this invention. Fundamental operations are the same as adopted in the above Example.

(1) Plasma dilution rate

A study on the relationship between the effect of PC inhibitor and plasma dilution rate has revealed that a linear relationship between plasma dilution rate and PC activity measured can be achieved if sample plasma is diluted by a factor of about 10 or higher. As the plasma dilution rate falls below this level, the action of PC inhibitor becomes more marked, with the curve deviating from linearity.

It is therefore preferable that the plasma sample be diluted by a factor of 10 or higher.

(2) $Ca^{2+}$ ion concentration

A test was made to determine the optimum $Ca^{2+}$ ion concentration for PC activation. It was demonstrated that the concentration of $Ca^{2+}$ in the buffer solution for diluting plasma should preferably be in the range of 0.1 to 4 mM, most preferably in the range of 0.5 to 2.5 mM.

(3) Amount of thrombin added

In the reaction system of the above Example, PC could be activated almost quantitatively by the use of 1 U or more of thrombin. The amount of thrombin to be added was set to 1 U in the kit of the above Example in order to minimize the amount of antithrombin/heparin to be used after activation of PC.

(4) Amount of thrombomodulin added

A test using different amounts of thrombomodulin revealed that PC could be sufficiently activated in the reaction system of the above Example if 0.04 nmol or more of thrombomodulin is added. The preferred amount is 0.06 to 0.16 nmol.

(5) Amount of Compound 1 added

A study using Compound 1 with different concentrations showed that the effect of interfering substances that act upon the synthetic substrate S-2366 (other than PCa) could be eliminated almost completely, if the concentration of Compound 1 in the solution is about 75 μg/ml or more.

A separate experiment using isolated and purified PC showed that use of Compound 1 with a concentration of 150 μg/ml or more can affect PC activity. Hence, Compound 1 should preferably be used at a concentration lower than 150 μg/ml.

It was experimentally verified that Compound 2 may be used in much the same way as with Compound 1. Compound 3, on the other hand, could inhibit the activity of interfering substances almost completely at its solution concentration of about 25 μg/ml.

PC activity and amounts of PC antigen in the plasma of normal persons, patients suffering a hepatic disease and patients suffering DIC were measured by the method of this invention and by the immunological method [EIA: J. C. Giddings et al., Brit. J. Haematol., 52, 495–502 (1982)]. The results are summarized in FIG. 2.

The PC activity data of the method of this invention were obtained from the calibration curve of FIG. 1 and are expressed in percentage.

Figure 2:
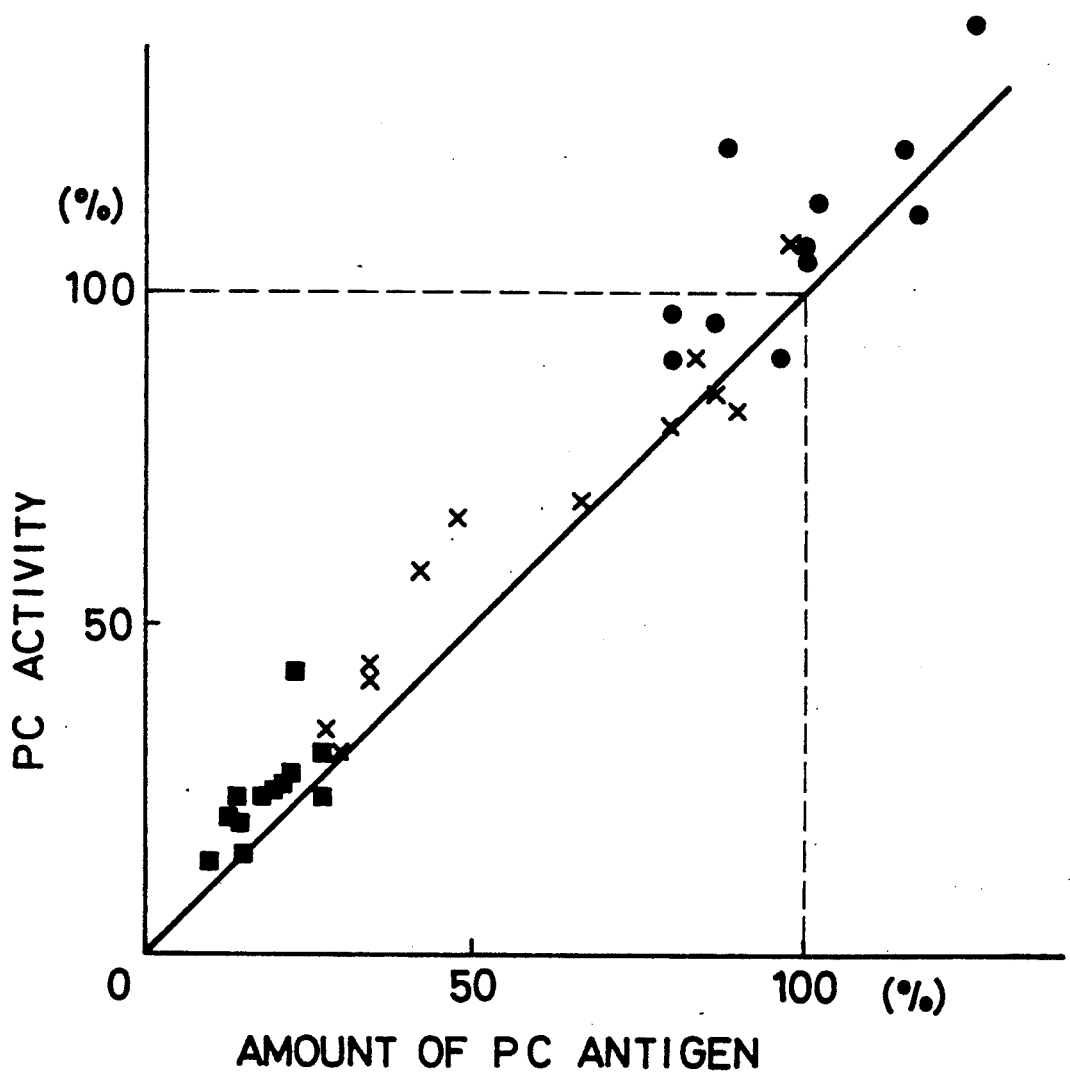

FIG. 2 clearly shows a good correlation between the PC activity measured by the method of this invention and the amount of PC antigen measured by the immunological method. This correlation holds not only for normal persons, but also for patients suffering from hepatitis and DIC in which the content of plasma PC is generally lower.

The method of this invention dispenses with the pretreatment for isolation of PC, which is indispensable in the conventional enzymatic methods and which requires much time and labor, thus allowing PC activity measurement by use of untreated plasma.

The volume of sample plasma required for each test is as small as 10 μl or less, and the amount of PC contained in it can be quantitatively determined in a short time by simple operations. The PC activity measured by the method of this invention correlates well with the amount of PC antigen measured by the immunological method, indicating the high accuracy of the method of this invention.

As is apparent from the foregoing, the method of this invention is very simple, accurate and rapid compared with the conventional methods, and is particularly suitable for treatment of a vast number of samples. It is therefore very useful for diagnosis of PC deficiency diseases, DIC and hepatitis, and for testing the efficacy of various coagulation factor (e.g., factor IX) preparations.

What is claimed is:

1. A method for assaying protein C (PC) comprising the steps of:
   making activated protein C (PCa) by adding PC activator to diluted plasma;
   adding antithrombin III, heparin and low-molecular-weight thrombin inhibitor;
   adding synthetic peptide substrate for activated protein C; and
   measuring colorimetrically or fluorometrically the amount of decomposition product formed by hydrolyses of the substrate with PCa.

2. The method for assaying PC as defined in claim 1, wherein the plasma is diluted with a buffer solution by a factor of from 10 to 30.

3. The method for assaying PC as defined in claim 1, wherein the low-molecular-weight thrombin inhibitor is of a molecular weight of less than or equal to 2000.

4. The method for assaying PC as defined in claim 3, wherein the thrombin inhibitor is an $N^2$-arylsulfonyl-L-argininamide.

5. The method for assaying PC as defined in claim 3, wherein the thrombin inhibitor is an N-arylsulfonylglycyl-amidinophenylalanine.

6. The method recited in claim 1, wherein said PC activator comprises thrombin and thrombomodulin.

7. A kit for measuring PC activity comprising (A) a thrombin and thrombomodulin, (B) an antithrombin III and heparin, (C) a low-molecular-weight thrombin inhibitor, and (D) a synthetic peptide substrate for activated protein.

8. The kit for measuring PC activity as defined in claim 7, wherein the low-molecular-weight thrombin inhibitor is of a molecular weight of less than or equal to 2000.

9. The kit for measuring PC activity as defined in claim 8, wherein the low-molecular-weight thrombin inhibitor is an $N^2$-arylsulfonyl-L-argininamide.

10. The kit for measuring PC activity as defined in claim 8, wherein the low-molecular-weight thrombin inhibitor is an N-arylsulfonylglycyl-amidinophenylalanine.

11. The kit for measuring PC activity as defined in claim 7, the kit further comprising a buffer solution for diluting plasma and a reaction terminator for terminating reaction of synthetic peptide substrate for activated protein C.

* * * * *